(12) United States Patent
Hwang et al.

(10) Patent No.: US 11,592,415 B2
(45) Date of Patent: Feb. 28, 2023

(54) BIO-SENSOR HAVING INTERDIGITATED MICROELECTRODE USING RESPONSE OF RECEPTOR AND TARGET BIOPRODUCTS

(71) Applicant: Korea Institute of Science and Technology, Seoul (KR)

(72) Inventors: Kyo Seon Hwang, Seoul (KR); Young Soo Kim, Seoul (KR); Jin Sik Kim, Seoul (KR); Yong Kyoung Yoo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 277 days.

(21) Appl. No.: 16/070,672

(22) PCT Filed: Oct. 20, 2016

(86) PCT No.: PCT/KR2016/011788
§ 371 (c)(1),
(2) Date: Jul. 17, 2018

(87) PCT Pub. No.: WO2017/115988
PCT Pub. Date: Jul. 6, 2017

(65) Prior Publication Data
US 2019/0025241 A1   Jan. 24, 2019

(30) Foreign Application Priority Data
Dec. 28, 2015 (KR) .................. 10-2015-0187388

(51) Int. Cl.
*G01N 27/327* (2006.01)
*G01N 27/12* (2006.01)
(Continued)

(52) U.S. Cl.
CPC ....... *G01N 27/3275* (2013.01); *G01N 27/126* (2013.01); *G01N 27/128* (2013.01);
(Continued)

(58) Field of Classification Search
CPC ............ G01N 27/3275; G01N 27/126; G01N 27/128; G01N 27/327; G01N 27/3272;
(Continued)

(56) References Cited

U.S. PATENT DOCUMENTS

2003/0085719 A1    5/2003   Yoon et al.
2005/0227373 A1*  10/2005   Flandre ................ G01N 27/221
                                                                   436/518
(Continued)

FOREIGN PATENT DOCUMENTS

KR   10-2003-0038084 A    5/2003
KR   10-2005-0103824 A   11/2005
(Continued)

OTHER PUBLICATIONS

Kim et al, Fabrication of comb interdigitated electrodes array (IDA) for a microbead-based electrochemical assay system, Nov. 2004, Biosensors and Bioelectronics, 20, p. 887-894 (Year: 2004).*

(Continued)

*Primary Examiner* — Matthew D Krcha
*Assistant Examiner* — Austin Q Le
(74) *Attorney, Agent, or Firm* — Rabin & Berdo, P.C.

(57) ABSTRACT

The present invention relates to an interdigitated microelectrode biosensor using the reaction between receptors and target biomaterials, the interdigitated microelectrode biosensor comprising: an insulating layer formed so as to cover all of the sensor formation area of a substrate; a first interdigitated microelectrode formed such that a plurality of first protruding electrodes are arranged in a comb shape on the insulating layer of the substrate; a second interdigitated microelectrode, facing the first interdigitated microelectrode and formed such that a plurality of second protruding electrodes are arranged in a comb shape on the insulating layer of the substrate such that the plurality of second (Continued)

protruding electrodes are arranged to respectively interdigitate with the plurality of first protruding electrodes formed at the first interdigitated microelectrode; and a plurality of receptors arranged in the space between the first and second interdigitated microelectrodes, which are arranged to interdigitate with each other, so as to specifically react with the target biomaterial, thereby increasing an impedance detection width and detection limit, and improving detection accuracy according to the characteristics of each monomer and each polymer.

3 Claims, 8 Drawing Sheets

(51) Int. Cl.
  *G01N 33/68*   (2006.01)
  *G01N 33/543*   (2006.01)
  *C08L 39/06*   (2006.01)
  *C08L 83/04*   (2006.01)

(52) U.S. Cl.
  CPC ....... *G01N 27/327* (2013.01); *G01N 27/3272* (2013.01); *G01N 33/543* (2013.01); *G01N 33/5438* (2013.01); *G01N 33/68* (2013.01); *C08L 39/06* (2013.01); *C08L 83/04* (2013.01); *C08L 2203/02* (2013.01); *C08L 2203/20* (2013.01)

(58) Field of Classification Search
  CPC .. G01N 33/543; G01N 33/5438; G01N 33/68; C08L 39/06; C08L 83/04; C08L 2203/02; C08L 2203/20; B01L 2300/0861; B01L 2300/088; B01L 2300/0883; B01L 3/5027
  See application file for complete search history.

(56) References Cited

U.S. PATENT DOCUMENTS

| | | | |
|---|---|---|---|
| 2005/0239120 A1 | 10/2005 | Park et al. | |
| 2008/0156661 A1* | 7/2008 | Cooper | ................ A61B 5/6848 |
| | | | 205/775 |
| 2009/0084686 A1* | 4/2009 | Yun | .................... G01N 33/5438 |
| | | | 205/792 |
| 2010/0193378 A1* | 8/2010 | Bratov | ............... G01N 27/3276 |
| | | | 205/792 |
| 2011/0024309 A1* | 2/2011 | Lee | .................... G01N 27/3276 |
| | | | 205/792 |
| 2013/0264221 A1 | 10/2013 | Kim et al. | |
| 2016/0238553 A1* | 8/2016 | Shachar | ............. G01N 27/4145 |

FOREIGN PATENT DOCUMENTS

| | | |
|---|---|---|
| KR | 10-0777973 B1 | 11/2007 |
| KR | 10-2009-0101764 A | 9/2009 |
| KR | 10-2012-0067967 A | 6/2012 |
| KR | 10-2015-0089226 A | 8/2015 |

OTHER PUBLICATIONS

Diaz-Gonzalez et al, Recent Advances in Electrochemical Enzyme Immunoassays, 2005, Electroanalysis, 17, 21, pp. 1901-1918 (Year: 2005).*

* cited by examiner

BIO-SENSOR HAVING INTERDIGITATED MICROELECTRODE USING RESPONSE OF RECEPTOR AND TARGET BIOPRODUCTS

TECHNICAL FIELD

The present invention relates to an interdigitated microelectrode biosensor, and more particularly, to an interdigitated microelectrode biosensor using the reaction between receptors and target biomaterials, wherein the receptors reacting specifically with the target biomaterials are located between interdigitated microelectrodes to increase the width of impedance detection and the limit of impedance detection and also to improve the accuracy of detection according to the characteristics of monomers and oligomers of the target biomaterials.

BACKGROUND ART

In recent years, many biosensors have been developed for detecting the presence and concentration of a variety of biological substances, such as genes and proteins, by electrical methods. One example is to use interdigitated microelectrodes. Since biosensors using interdigitated microelectrodes have a very substantially broad region in a zigzag configuration where receptors capable of binding specifically to biological substances are immobilized, they are praised for their ability to measure even a low concentration of the biological substances.

Such a biosensor using interdigitated microelectrodes is disclosed in Korean Patent No. 777973 (published on Nov. 29, 2007). According to this patent, since the concentration of a biological substance is measured based on an electric current flowing between the electrodes, it is necessary to use conductive particles for the flow of electric current between the electrodes. However, the use of the conductive particles is troublesome.

Further, the biosensor has the problem that a larger amount of an electric field having an influence on the impedance between the electrodes escapes upward from the electrodes than the amount generated between the electrodes. That is to say, the impedance variation is more affected by changes generated above the electrodes than by reactions generated between the electrodes. As a result, a narrow width and a low limit of impedance detection as well as a low accuracy of impedance detection are obtained, thereby implying poor reliability and availability of the biosensor.

PRIOR ART DOCUMENT (Patent document 1) Korean Patent No. 777973 (published on Nov. 29, 2007)

DISCLOSURE

Technical Problem

Accordingly, the present invention has been made in view of the above-mentioned problems occurring in the prior art, and it is an object of the present invention to provide an interdigitated microelectrode biosensor using the reaction between receptors and target biomaterials, wherein the receptors reacting specifically with the target biomaterials are located between interdigitated microelectrodes, without having any conductive particles adapted to allow electric current to flow between the interdigitated microelectrodes, thereby increasing the width of impedance detection and the limit of impedance detection and also improving the accuracy of detection according to the characteristics of monomers and oligomers of the target biomaterials.

Technical Solution

To accomplish the above-mentioned object, according to the present invention, there is provided an interdigitated microelectrode biosensor including: an insulating layer adapted to cover all of a biosensor formation region of a substrate; a first interdigitated microelectrode having a plurality of first protrusion electrodes arranged in a comb-like shape on the insulating layer of the substrate; a second interdigitated microelectrode facing the first interdigitated microelectrode and having a plurality of second protrusion electrodes arranged in a comb-like shape on the insulating layer of the substrate in such a manner as to be interdigitated with the first protrusion electrodes of the first interdigitated microelectrode; and a plurality of receptors arranged in the space between the first interdigitated microelectrode and the second interdigitated microelectrode arranged interdigitatedly with each other so as to react specifically with target biomaterials.

Advantageous Effects

According to the present invention, the interdigitated microelectrode biosensor using the reaction between the receptors and the target biomaterials is configured to locate the receptors reacting specifically with the target biomaterials between the interdigitated microelectrodes, without having any conductive particles adapted to allow electric current to flow between the interdigitated microelectrodes, and configured to permit the adjacent interdigitated microelectrodes to face each other, so that the electric field is prevented from escaping upward from the interdigitated microelectrodes, thereby increasing the width of impedance detection by tens to hundreds of times and improving the accuracy of the detection.

In addition, the interdigitated microelectrode biosensor according to the present invention is configured to locate the receptors reacting specifically with the target biomaterials on the insulating layer between the respective interdigitated microelectrodes, so that the accuracy of detection can be improved according to the characteristics of the monomers and oligomers of the target biomaterials.

BEST MODE FOR INVENTION

Embodiments of the present invention will now be described in more detail with reference to the attached drawings.

Figure 1:
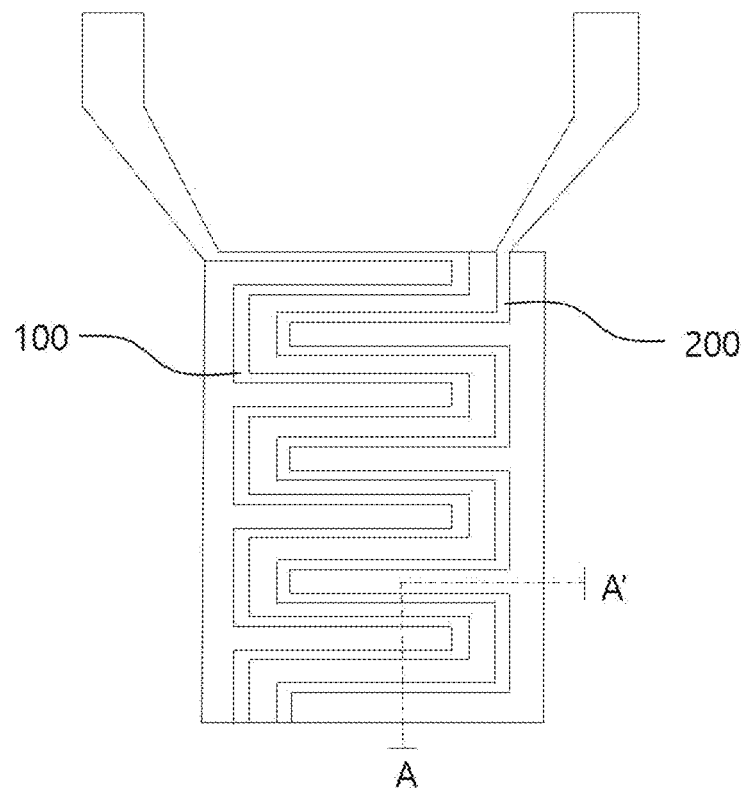
FIG. 1 illustrates a configuration of an interdigitated microelectrode biosensor using the reaction between receptors and target biomaterials according to the present invention.
Figure 2:
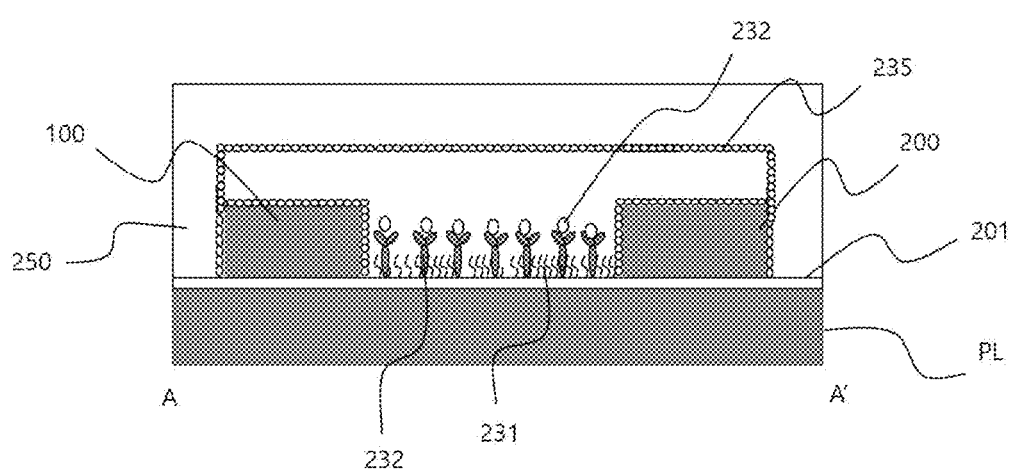
FIG. 2 is a sectional view taken along the line A-A of FIG. 1, which illustrates an interdigitated microelectrode biosensor according to a first embodiment of the present invention.

FIG. 1 illustrates a configuration of an interdigitated microelectrode biosensor using the reaction between receptors and a target biomaterial according to the present invention, and FIG. 2 is a sectional view taken along the line A-A of FIG. 1, which illustrates an interdigitated microelectrode biosensor according to a first embodiment of the present invention. Further, FIG. 3 shows detailed configurations and actual shapes of the interdigitated microelectrodes of FIG. 2.

Figure 3:
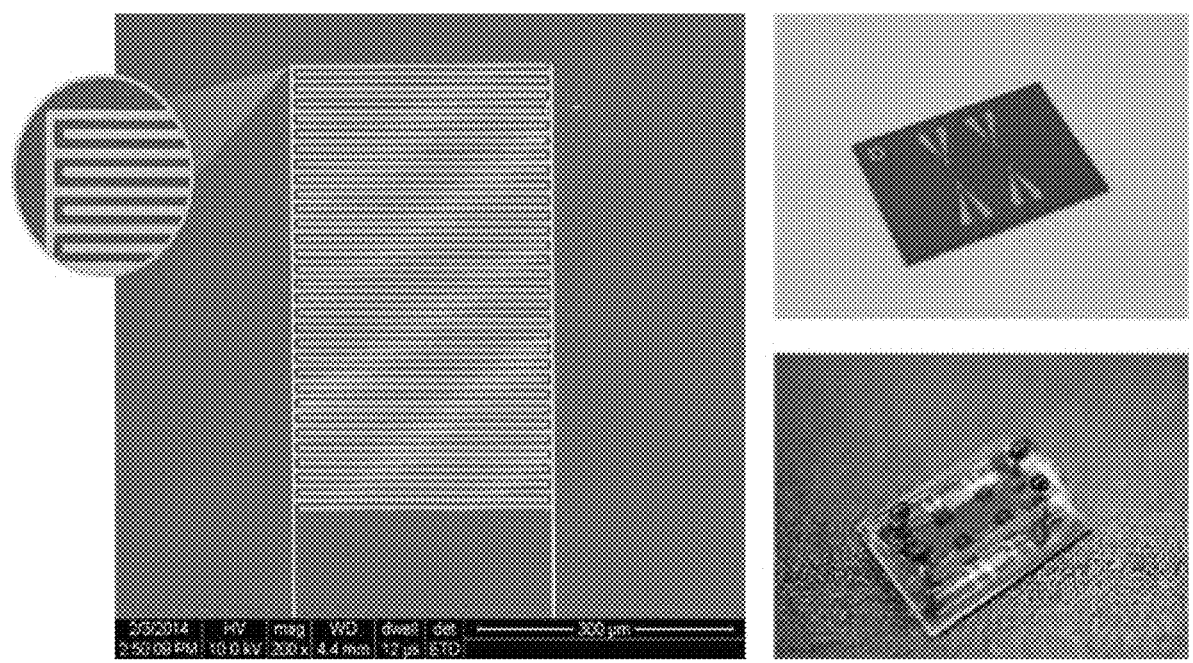
FIG. 3 shows detailed configurations and actual shapes of the interdigitated microelectrodes of FIG. 2.

As shown in FIGS. 1 to 3, an interdigitated microelectrode biosensor according to the present invention includes: a first interdigitated microelectrode 100 having a plurality of first protrusion electrodes arranged in a comb-like shape on a substrate PL; a second interdigitated microelectrode 200 facing the first interdigitated microelectrode 100 and having a plurality of second protrusion electrodes arranged in a comb-like shape on the substrate PL in such a manner as to be interdigitated with the first protrusion electrodes of the first interdigitated microelectrode 100; and a plurality of receptors 231 arranged in the space between the first interdigitated microelectrode 100 and the second interdigitated microelectrode 200 interdigitatedly arranged with each other so as to react specifically with target biomaterials 232. In this case, the receptors 231 include at least one of beta-amyloid antibodies, aptamers, and peptides.

First, the detection of impedance through the interdigitated microelectrode biosensor using the reaction with the target biomaterials 232 will be explained. The impedance between the first interdigitated microelectrode 100 and the second interdigitated microelectrode 200 is summarized as follows:

$$Z = R + jX$$
$$= R + j(XL - XC)$$
$$= R - jXC$$
$$= R - j(1/wC)$$

wherein Z is impedance, R is resistance, X is reactance, C is capacitance, and w is angular frequency. The reactance X is divided into inductor component XL and capacitor component XC. The inductor component XL is ignored and only the capacitor component XC remains because the first interdigitated microelectrode 100 is not directly connected electrically to the second interdigitated microelectrode 200.

Accordingly, the plurality of receptors 231 are immobilized in the space between the first interdigitated microelectrode 100 and the second interdigitated microelectrode 200, and at the time when the target biomaterials 232 react with the receptors 231, if the variation of impedance in the space between the first interdigitated microelectrode 100 and the second interdigitated microelectrode 200, that is, in the space between the first interdigitated microelectrode 100 and the second interdigitated microelectrode 200 facing each other, quantitative analysis of the target biomaterials 232 can be obtained.

As shown in FIGS. 1 and 2, if the plurality of receptors 231 are immobilizedly arranged in the space between the first interdigitated microelectrode 100 and the second interdigitated microelectrode 200, generally, variations in electric field and impedance occur in a horizontal direction along which the first interdigitated microelectrode 100 and the second interdigitated microelectrode 200 are arranged in the state of placing the plurality of receptors 231 therebetween.

Figure 4:
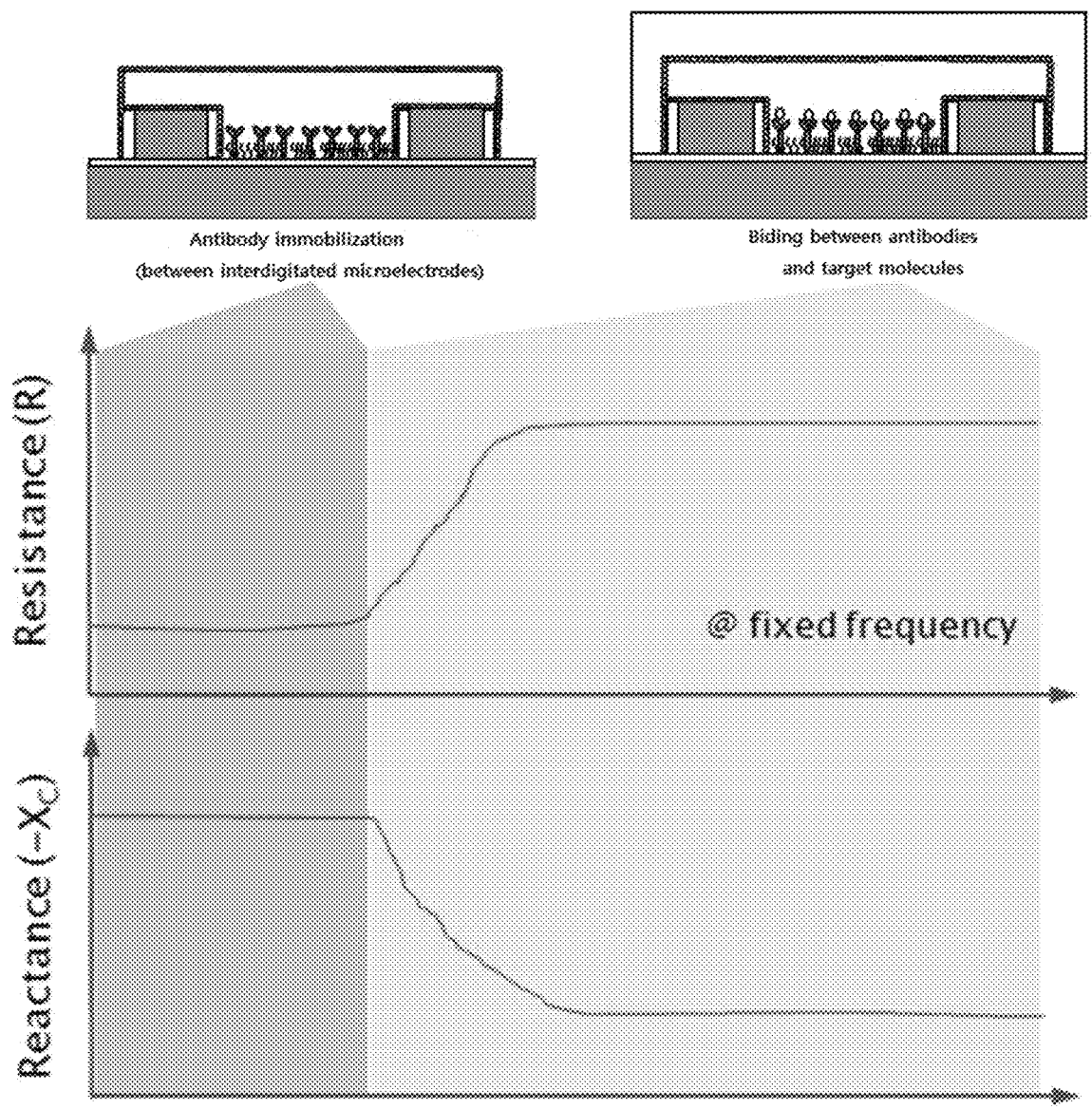
FIG. 4 is a graph showing a variation in the impedance of the interdigitated microelectrode biosensor through the reaction between antibodies and target biomaterials.

FIG. 4 is a graph showing a variation in the impedance of the interdigitated microelectrode biosensor through the reaction between antibodies and target biomaterials.

As shown in FIG. 4, if the plurality of receptors 231 bind specifically to the target biomaterials 232, a variation in resistance occurs between the first interdigitated microelectrode 100 and the second interdigitated microelectrode 200 because the target biomaterials 232 are located therebetween. Further, the capacitance C decreases due to the properties of the target biomaterials, resulting in an increase in reactance Xc and a decrease in −Xc. The amount of the target biomaterials 232 can be exactly detected by measuring the resistance and reactance variations.

If the inductor component is ignored and only the reactance having the capacitor component is considered, like this, it is easy to check the variation in impedance only when a driving frequency is high, and contrarily, if the driving frequency is low, it is hard to check the variation in impedance because the variation is very weak. So as to detect a small amount of target biomaterials 232, therefore, high driving frequency should be used.

If the driving frequency is high, however, electric current generally flows through the space above the target biomaterials 232 binding specifically to the receptors 231, so that the detection of the target biomaterials 232 cannot be detected well. If the driving frequency is high, in addition, the target biomaterials 232 may be damaged by the high driving frequency, so that they are not detected well.

So as to detect the target biomaterials 232 well, accordingly, a low driving frequency in a range of 10 to 100 Hz is used. Because the driving frequency is low, accordingly, the damage on the target biomaterials 232 can be desirably prevented. Of course, it is hard to detect minute impedance variations because of the low frequency, but such a difficulty can be solved by means of the adoption of a differential amplifier.

In case where the conventional interdigitated microelectrode biosensor is used to detect biomaterials, antibodies are immobilized on tops and sides of the microelectrodes and the surrounding portions of the microelectrodes, and next, an impedance variation at the time when the antibodies bind to target molecules is observed. In this case, the antibodies are immobilized two-dimensionally only on the surfaces of the microelectrodes. According to an embodiment of the present invention, however, the receptors 231 and the antibodies are disposed only between the first interdigitated microelectrode 100 and the second interdigitated microelectrode 200, and in this case, an amount of electric field discharged to the outside can be reduced. Further, the receptors 231 and the antibodies are immobilized on a region where the electric field is concentrated, thereby extending the accuracy and dynamic range of the biosensor. According to the present invention, particularly, in case where the target biomaterials 232 are detected with the low driving frequency in the range of 10 to 100 Hz, a gap between the two microelectrodes 100 and 200 is desirably in a range of 3 to 7 μm. If the gap is less than 3 μm, a deviation in detected signals is too high, thereby failing to provide a reliable test, and if the gap is greater than 7 μm, sensitivity decreases to cause a difficulty in detecting a small amount of target biomaterials 232. When considering the deviation and sensitivity, most desirably, the gap is 5 μm.

Figure 5:
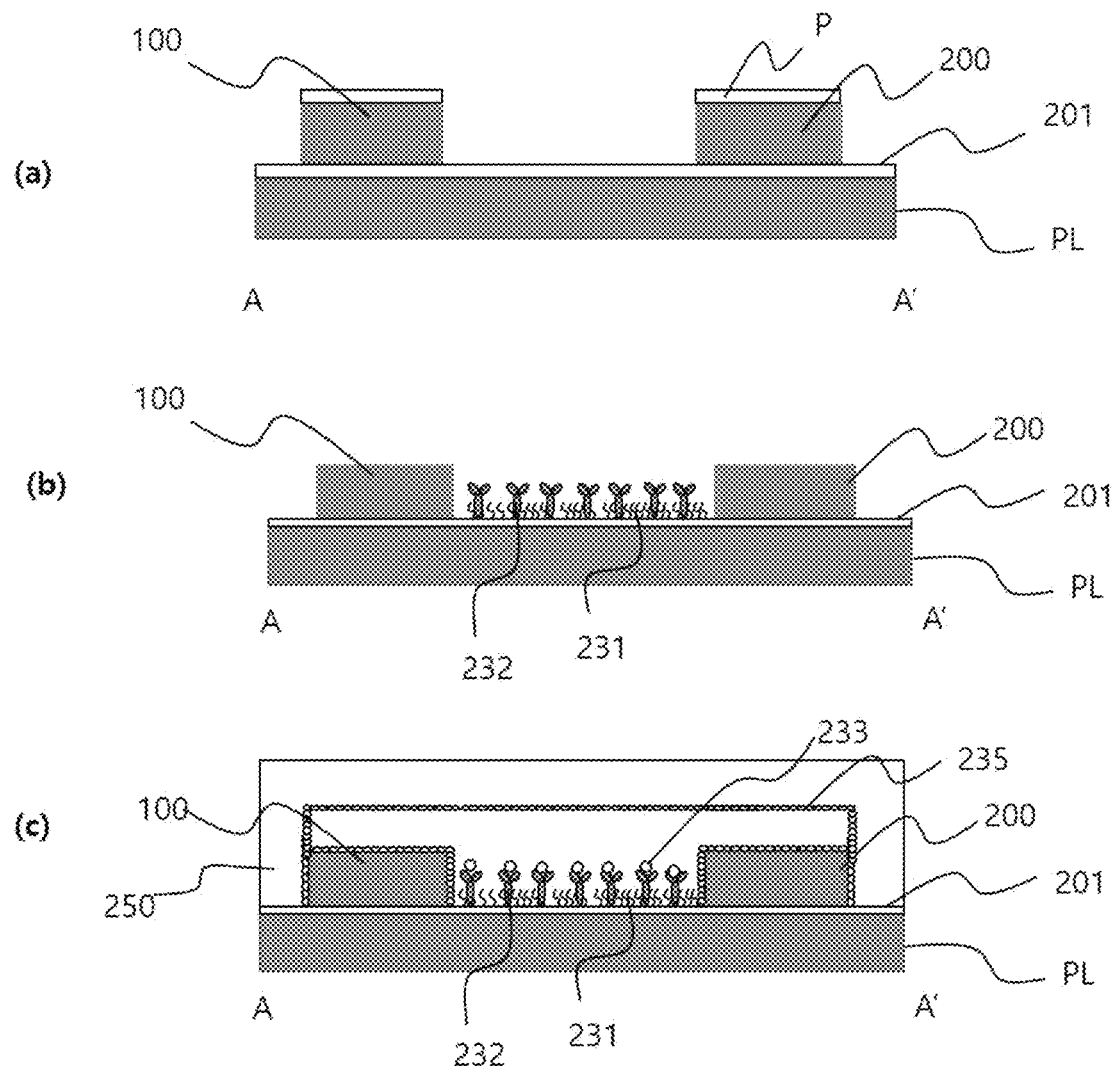
FIGS. 5a to 5c are sectional views showing a method for manufacturing the interdigitated microelectrode biosensor illustrated in FIGS. 1 to 3 according to the first embodiment of the present invention.

FIGS. 5a to 5c are sectional views showing a method for manufacturing the interdigitated microelectrode biosensor illustrated in FIGS. 1 to 3 according to the first embodiment of the present invention.

So as to form an insulating layer 201, as shown in FIG. 5a, a 500 nm thick silicon dioxide ($SiO_2$) is formed on the substrate PL by means of thermal oxidation, and next, titanium (Ti) having a thickness in the range of 30 to 50 nm and platinum (Pt) having a thickness in the range of 150 to 200 nm are sequentially deposited on the silicon dioxide layer by means of sputtering, thereby forming metal layers. The titanium (Ti) layer and the platinum (Pt) layer are used as adhesion layers to increase the bonding strength of the silicon dioxide layer. The substrate on which $SiO_2$/Ti/Pt are deposited in this order is provided with a photoresist micropatterned through photolithography.

Subsequently, the multi-layer thin film deposition substrate having the micropatterned photoresist is allowed to sequentially etch the titanium (Ti) layer and the platinum (Pt) layer through inductively coupled plasma reactive ion etcher (ICP-RIE) to form the two microelectrodes 100 and 200 with the metal patterns, and after that, the photosensitive film patterns formed thereon are removed.

As shown in FIG. 5b, next, a surface treatment process is performed, and at the surface treatment process, a calix-crown self-assembled monolayer or a polyvinylpyrrolodone (PVP) surface modification layer, as a connection molecular layer 233 adapted to selectively immobilize beta-amyloid antibodies, is formed on the surface of the insulating layer 201 between the first interdigitated microelectrode 100 and the second interdigitated microelectrode 200. After that, the beta-amyloid antibodies as the receptors 231 are immobilized onto the connection molecular layer 233. If so, the beta-amyloids as the target biomaterials 232 selectively bind specifically to the receptors 231.

In this case, a reference electrode for the signal comparison of the interdigitated microelectrode biosensor on which the beta-amyloid antibodies are immobilized and an interdigitated microelectrode biosensor on which prostate-specific antigen (PSA) antibodies are immobilized for negative control are provided.

Subsequently, if a region where the target biomaterials 232 bind specifically is completely exposed to the outside, detection errors may happen, and accordingly, there is a need to cover the region. To do this, a protection cap 250 is desirably disposed above the first interdigitated microelectrode 100 and the second interdigitated microelectrode 200. Further, a polydimethylsiloxane (PDMS) chip having two microchannels is attached to prevent non-specific binding to other materials except the beta-amyloid, and an absorption prevention layer (bovine serum albumin) 235 is coated on the entire portion except the microchannels and a portion where the antibodies of the interdigitated microelectrode biosensor are immobilized, that is, on the inner wall of the protection cap 250 and the surfaces of the first interdigitated microelectrode 100 and the second interdigitated microelectrode 200 except the portion where the receptors 231 are not immobilized.

So as to perform stabilization, additionally, 0.1× phosphate-buffered saline (PBS) is injected into the two microchannels, and while an impedance signal of the interdigitated microelectrode biosensor is being observed until it is maintained stably and constantly, the stabilization is desirably performed. Initial stabilization time is given for five minutes to the biosensor whose stabilization is finished, and 10 pg/ml beta-amyloid is injected into the microchannels to observe the impedance signal for about 15 minutes, thereby checking the antigen-antibody reaction of the beta-amyloid. So as to minimize the non-specific binding or the influence of the electrical signal caused by the biomaterials existing in the PBS solution, after that, a clean PBS solution is injected to perform a solution change. Next, the impedance variation is observed for five minutes, thereby checking the size of a final signal through the specific reaction between the beta-amyloid and the antibodies.

Figure 6:
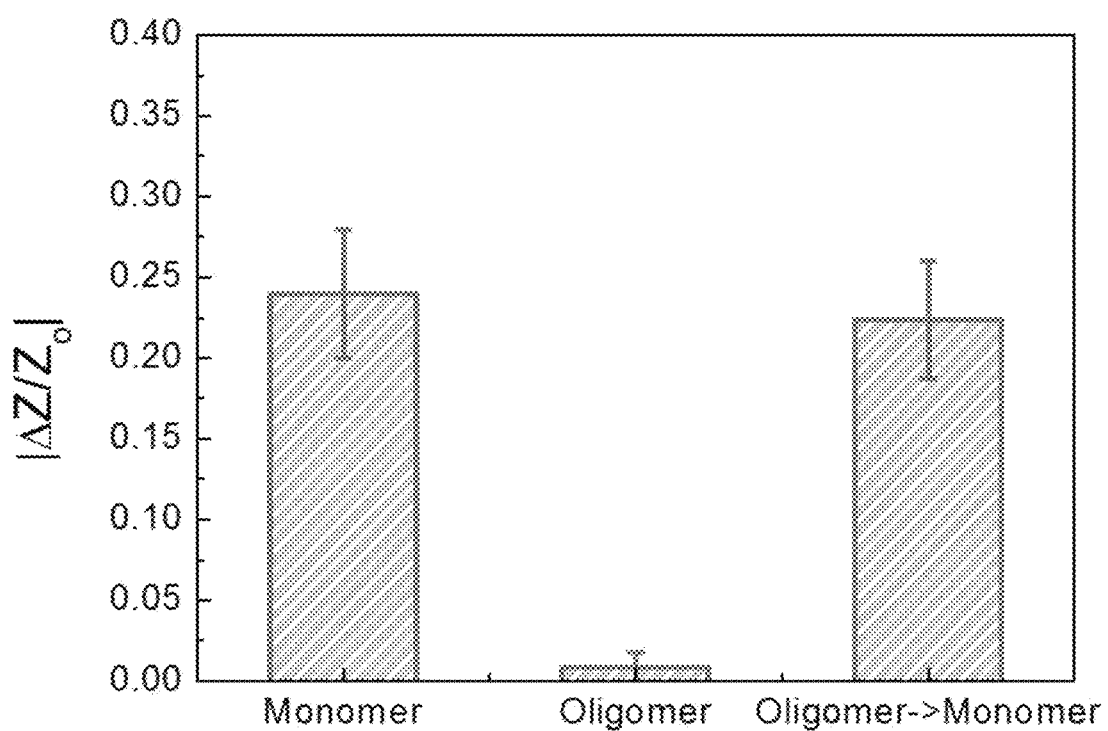
FIG. 6 is a graph showing signal sizes of the interdigitated microelectrode biosensor when beta-amyloid monomers, beta-amyloid oligomers, and beta-amyloid monomers monomerized from beta-amyloid oligomers, which have the same concentrations as each other, react.

FIG. 6 is a graph showing signal sizes of the interdigitated microelectrode biosensor when a beta-amyloid monomer, a beta-amyloid oligomer, and a beta-amyloid monomer monomerized from beta-amyloid oligomer, which have the same concentrations as each other, react.

As shown in FIGS. 1 to 3, the interdigitated microelectrode biosensor can distinguish the monomers of protein and the oligomers of protein from each other. As shown in FIG. 6, a 100 pg/mL beta-amyloid monomer and a 100 pg/mL beta-amyloid oligomer are provided to have the same concentration as each other. Further, the 100 pg/mL beta-amyloid monomer is left at a room temperature for six hours and thus oligomerized, and next, when the oligomerized beta-amyloid monomer is injected into the interdigitated microelectrode biosensor where the beta-amyloid antibodies are formed, it is checked that the signal size of the monomer is greater by about 30 times than the oligomer. This is because the detection principle of the interdigitated microelectrode biosensor is determined upon the number of proteins binding to the antibodies and the sizes occupied by the proteins. After the oligomerized sample is monomerized through the injection of a detergent (e.g., epps) thereinto, the reaction is detected, and in this case, the monomerized sample has a very similar value to the value detected by using the sample only with the monomer, so that it is checked that the oligomer is generally monomerized.

Figure 7:
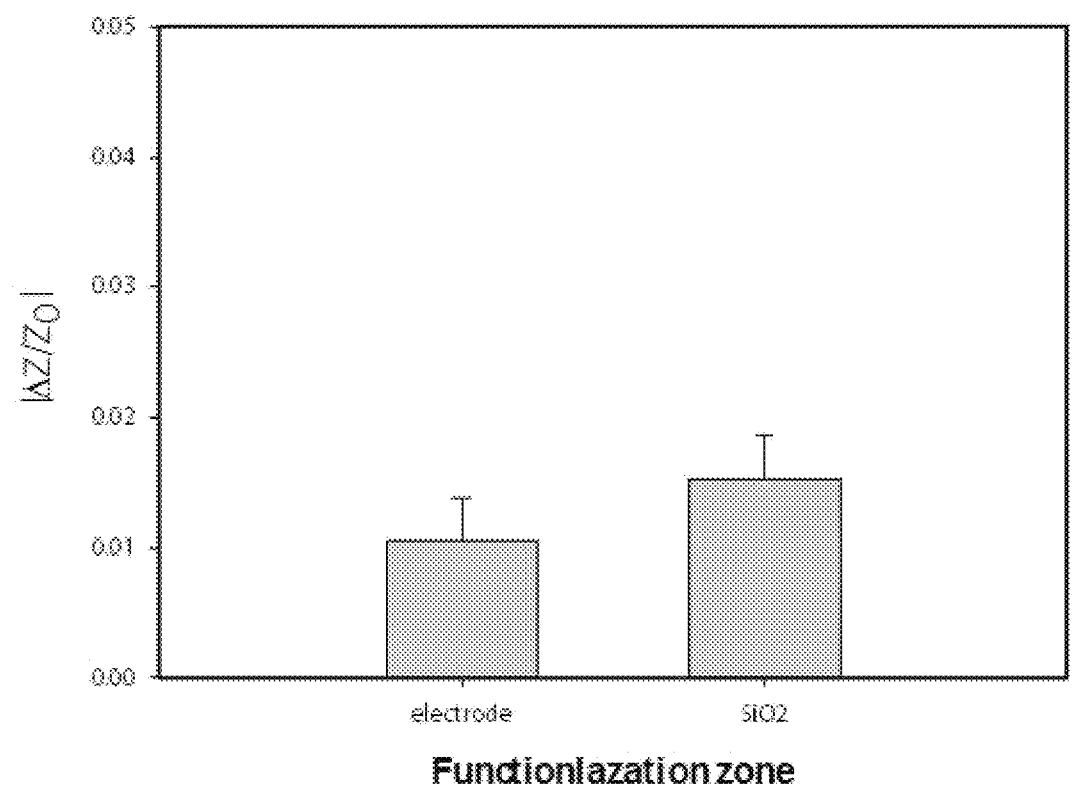
FIG. 7 is a graph showing sizes of target detection signals according to the functionalization zone of the interdigitated microelectrode biosensor illustrated in FIGS. 1 to 3.

FIG. 7 is a graph showing sizes of target detection signals according to the functionalization zone of the interdigitated microelectrode biosensor illustrated in FIGS. 1 to 3.

The interdigitated microelectrode biosensor as shown in FIGS. 1 to 3 has a principle wherein the plurality of receptors 232 formed of the antibodies or aptamers are immobilized on the surface of the silicon dioxide ($SiO_2$) layer as the insulating layer between the first interdigitated microelectrode 100 and the second interdigitated microelectrode 200 so as to detect target molecules existing in the sample. In this case, when compared with the existing detection through functionalization above the electrodes, the detection according to the present invention is more excellent in sensitivity, and as shown in FIG. 7, when compared with the detection signals at the time when the first interdigitated microelectrode 100 and the second interdigitated microelectrode 200 are functionalized, the detection signals according to the present invention are more increased by about 60%.

Figure 8:
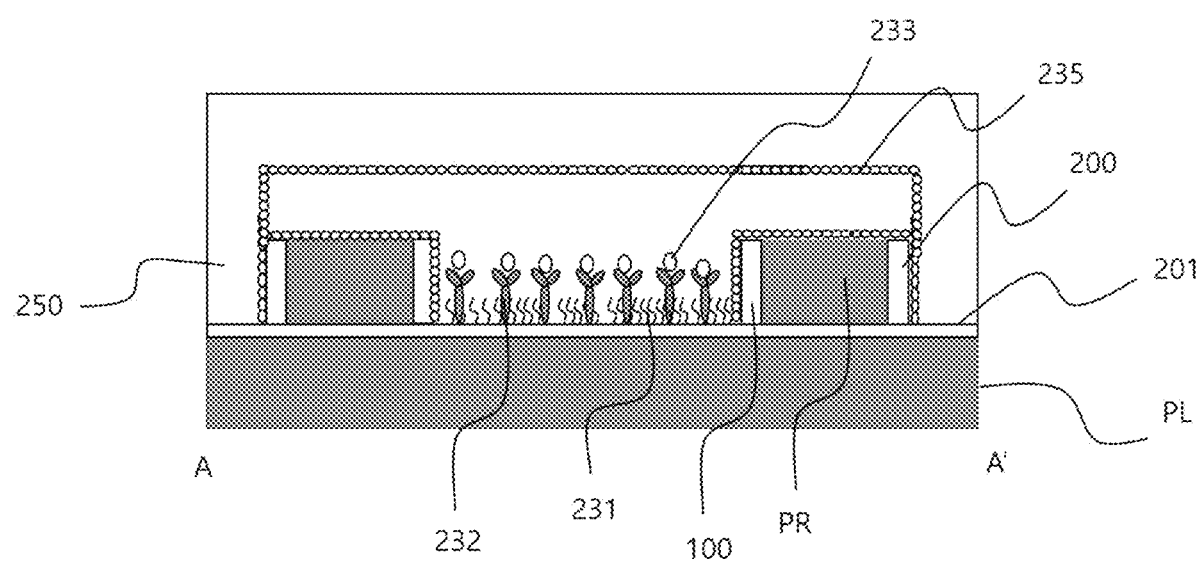
FIG. 8 is a sectional view taken along the line A-A of FIG. 1, which illustrates an interdigitated microelectrode biosensor according to a second embodiment of the present invention.

FIG. 8 is a sectional view taken along the line A-A of FIG. 1, which illustrates an interdigitated microelectrode biosensor according to a second embodiment of the present invention.

As shown in FIG. 8, an interdigitated microelectrode biosensor according to a second embodiment of the present invention includes: a first interdigitated microelectrode 100 having a plurality of first protrusion electrodes arranged in a comb-like shape on a substrate PL; a second interdigitated microelectrode 200 facing the first interdigitated microelectrode 100 and having a plurality of second protrusion electrodes arranged in a comb-like shape on the substrate PL in such a manner as to be interdigitated with the plurality of first protrusion electrodes arranged in the first interdigitated microelectrode 100; and a plurality of receptors 231 immobilized in the space between the first interdigitated microelectrode 100 and the second interdigitated microelectrode 200 arranged interdigitatedly with each other so as to react specifically with target biomaterials.

In detail, pattern of the first interdigitated microelectrode 100 and the second interdigitated microelectrode 200 are formed in comb-like shapes on the substrate PL, by a photolithography process using a photoresist, polymer, or silicon structure, and next, patterning for them is also carried out by the photolithography process to form metal patterns 210a surrounding both sides of the patterns of the first interdigitated microelectrode 100 and the second interdigitated microelectrode 200.

The formation of the plurality of receptors 231 in the space between the first interdigitated microelectrode 100 and the second interdigitated microelectrode 200 allows electric field and impedance variations to occur predominantly in the horizontal direction in which the first interdigitated microelectrode 100 and the second interdigitated microelectrode 200 are arranged in the state of placing the plurality of receptors 231 therebetween. With this arrangement, an electric field and an impedance are prevented from escaping upward from or perpendicularly to the first interdigitated microelectrode 100 and the second interdigitated microelectrode 200, and they are generated in the horizontal direction, so that the reaction efficiencies of the plurality of receptors 231 immobilized between the first interdigitated microelectrode 100 and the second interdigitated microelectrode 200 can be enhanced and the width of impedance detection can be improved by tens to hundreds of times.

Figure 9:
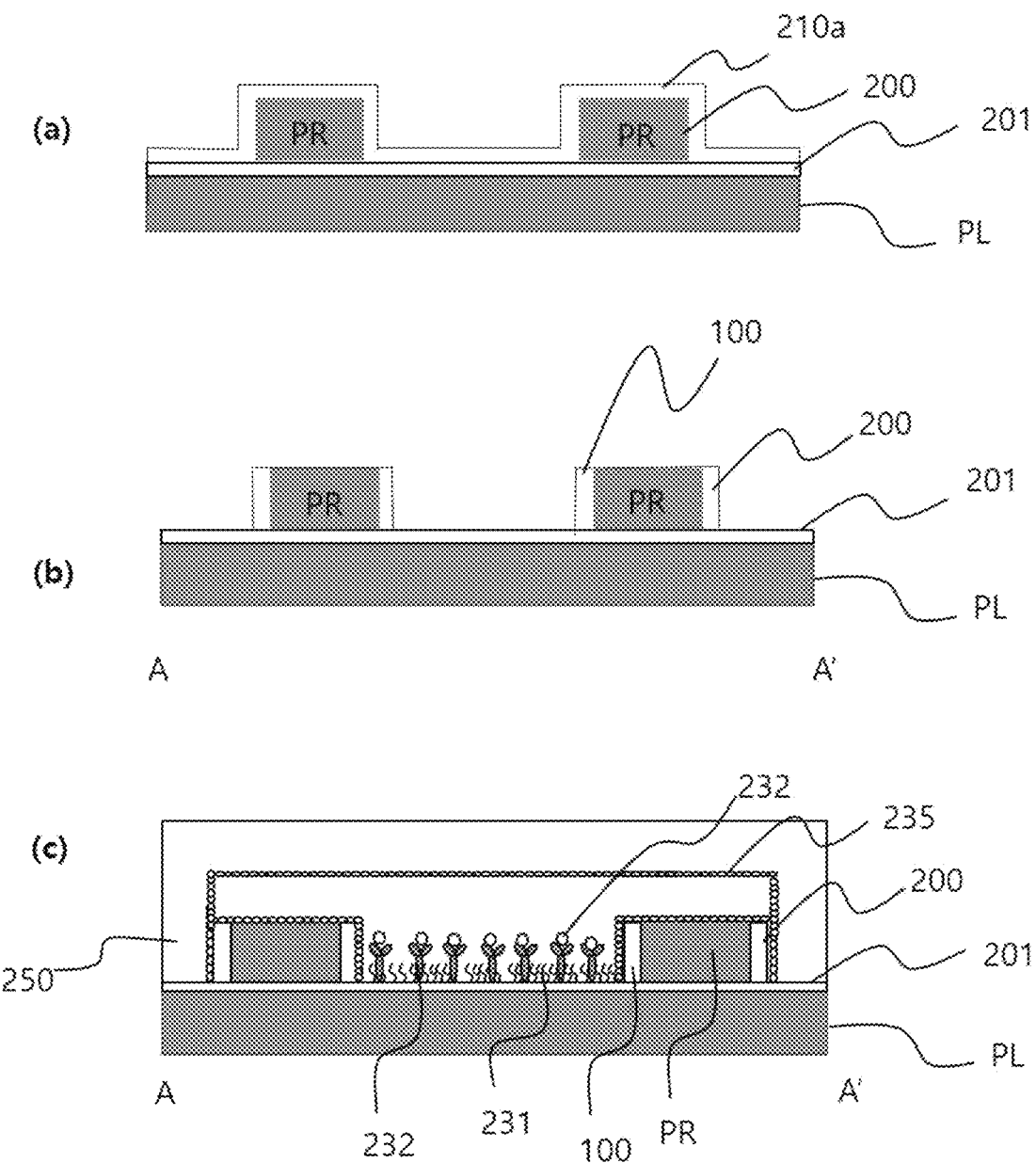
FIGS. 9a to 9c are sectional views showing a method for manufacturing the interdigitated microelectrode biosensor illustrated in FIGS. 1 to 3 according to the second embodiment of the present invention.

FIGS. 9a to 9c are sectional views showing a method for manufacturing the interdigitated microelectrode biosensor illustrated in FIGS. 1 to 3 according to the second embodiment of the present invention.

According to the patterning method using the photoresist, polymer, and the silicon structure, as shown in FIG. 9a, a 300 nm thick silicon dioxide ($SiO_2$) is deposited on the substrate (Si wafer) PL made of silicon by means of PECVD, thereby forming an insulating layer 201. So as to form the insulating layer 201, otherwise, a 500 nm thick silicon dioxide ($SiO_2$) is deposited on the substrate (Si wafer) PL made of silicon by means of thermal oxidation.

So as to form patterns of the first interdigitated microelectrode 100 and the second interdigitated microelectrode 200, further, a photoresist PR is micropatterned. So as to form the microelectrodes with metal patterns 210, after that, titanium (Ti) having a thickness in the range of 30 to 50 nm and platinum (Pt) having a thickness in the range of 150 to 200 nm are sequentially deposited on the silicon dioxide layer by means of sputtering. In this case, the titanium (Ti) layer and the platinum (Pt) layer are used as adhesion layers to increase the bonding strength of the silicon dioxide layer. The substrate on which SiO2/Ti/Pt are deposited in this order is provided with the photoresist micropatterned through photolithography.

Subsequently, as shown in FIG. 9b, the multi-layer thin film deposition substrate having the micropatterned photoresist is allowed to sequentially etch the titanium (Ti) layer and the platinum (Pt) layer through inductively coupled plasma reactive ion etcher (ICP-RIE) to form the two microelectrodes 100 and 200 with the metal patterns 210.

As shown in FIG. 9c, next, a surface treatment process is performed, and at the surface treatment process, a calix-crown self-assembled monolayer or a polyvinylpyrrolodone (PVP) surface modification layer, as a connection molecular layer 233 adapted to selectively immobilize the beta-amyloid antibodies, is formed on the surface of the insulating layer 201 between the first interdigitated microelectrode 100 and the second interdigitated microelectrode 200. After that, the beta-amyloid antibodies as the receptors 231 are immobilized onto the connection molecular layer 233. If so, the beta-amyloids as the target biomaterials 232 selectively bind specifically to the receptors 231. In this case, a reference electrode for the signal comparison of the interdigitated microelectrode biosensor on which the beta-amyloid antibodies are immobilized and an interdigitated microelectrode biosensor on which prostate-specific antigen (PSA) antibodies are immobilized for negative control are provided.

Subsequently, if a region where the target biomaterials 232 bind specifically is completely exposed to the outside, detection errors may happen, and accordingly, there is a need to cover the region. To do this, a protection cap 250 is desirably disposed above the first interdigitated microelectrode 100 and the second interdigitated microelectrode 200. Further, a polydimethylsiloxane (PDMS) chip having two microchannels is attached to prevent non-specific binding to other materials except the beta-amyloids, and an absorption prevention layer (bovine serum albumin) 235 is coated on the entire portion except the microchannels and a portion where the antibodies of the interdigitated microelectrode biosensor are immobilized, that is, on the inner wall of the protection cap 250 and the surfaces of the first interdigitated microelectrode 100 and the second interdigitated microelectrode 200 except the portion where the receptors 231 are not immobilized.

So as to perform stabilization, additionally, 0.1× phosphate-buffered saline (PBS) is injected into the two microchannels, and while an impedance signal of the interdigitated microelectrode biosensor is being observed until it is maintained stably and constantly, the stabilization is desirably performed. Initial stabilization time is given for five minutes to the biosensor whose stabilization is finished, and 10 pg/ml beta-amyloid is injected into the microchannels to observe the impedance signal for about 15 minutes, thereby checking the antigen-antibody reaction of the beta-amyloid. So as to minimize the non-specific binding or the influence of the electrical signal caused by the biomaterials existing in the PBS solution, after that, a clean PBS solution is injected to perform a solution change. Next, the impedance variation is observed for five minutes, thereby checking the size of a final signal through the specific reaction between the beta-amyloids and the antibodies.

As set forth in the foregoing, the interdigitated microelectrode biosensor using the reaction between the receptors and the target biomaterials is configured to locate the receptors reacting specifically with the target biomaterials between the interdigitated microelectrodes, without having any conductive particles adapted to allow electric current to flow between the interdigitated microelectrodes, and configured to permit the adjacent interdigitated microelectrodes to face each other, so that the electric field is prevented from escaping upward from the interdigitated microelectrodes, thereby increasing the width of impedance detection by tens to hundreds of times and improving the accuracy of the detection.

In addition, the interdigitated microelectrode biosensor according to the present invention is configured to locate the receptors specifically reacting with the target biomaterials on the insulating layer between the respective interdigitated microelectrodes, so that the accuracy of detection can be improved according to the characteristics of the monomers and oligomers of the target biomaterials.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An interdigitated microelectrode biosensor consisting of:
    an insulating layer formed on a substrate;
    a first interdigitated microelectrode having a plurality of first protrusion electrodes arranged in a comb-like shape on a surface of the insulating layer formed on the substrate;
    a second interdigitated microelectrode facing the first interdigitated microelectrode and having a plurality of second protrusion electrodes arranged in a comb-like shape on the surface of the insulating layer formed on the substrate in such a manner as to be interdigitated with the first protrusion electrodes of the first interdigitated microelectrode;
    a plurality of receptors directly immobilized on the surface of the insulating layer and arranged in a space between the first interdigitated microelectrode and the second interdigitated microelectrode arranged interdigitatedly with each other so as to react specifically with target biomolecules, wherein the target biomolecules do not electrically connect the first interdigitated microelectrode and the second interdigitated microelectrode;
    a connection molecular layer directly formed on surface of the insulating layer and placed between the first interdigitated microelectrode and the second interdigitated microelectrode to immobilize the plurality of receptors,
    wherein the first interdigitated microelectrode, the second interdigitated microelectrode, and the connection molecular layer are formed on the surface of the insulating layer,
    wherein the first interdigitated microelectrode and the second interdigitated microelectrode comprise:
        a first interdigitated microelectrode pattern and a second interdigitated microelectrode pattern formed by patterning carried out by at least one of a photoresist, a polymer and a silicon structure on the insulating layer formed on the substrate; and
        microelectrodes formed to surround only both sides of the first interdigitated microelectrode pattern and the second interdigitated microelectrode pattern in such a manner as to face each other,
    wherein the first and second interdigitated microelectrodes are configured such that resistance and reactance between the first interdigitated microelectrode and the second interdigitated microelectrode increase in response to the target biomolecules binding specifically to the plurality of receptors;
    a protection cap adapted to cover all of the substrate, the first interdigitated microelectrode, and the second interdigitated microelectrode;
    an absorption prevention layer coated on an inner wall of the protection cap and the surfaces of the first interdigitated microelectrode and the second interdigitated microelectrode except a portion where the receptors are not immobilized; and
    a polydimethylsiloxane (PDMS) chip configured to prevent non-specific binding to other materials except beta-amyloids.

2. The interdigitated microelectrode biosensor according to claim 1, wherein the connection molecular layer is a calix-crown self-assembled monolayer or a polyvinylpyrrolidone (PVP) surface modification layer adapted to selectively immobilize beta-amyloid antibodies, and the receptors comprise at least one of beta-amyloid antibodies, aptamers, and peptides.

3. The interdigitated microelectrode biosensor according to claim 1, wherein the receptors comprise at least one of beta-amyloid antibodies, aptamers, and peptides and are immobilized on the surface of the insulating layer formed on the substrate exposed to the space between the first interdigitated microelectrode and the second interdigitated microelectrode arranged interdigitatedly with each other in such a manner as to react specifically with the target biomolecules.

* * * * *